United States Patent [19]

Temple et al.

[11] Patent Number: 4,600,716
[45] Date of Patent: Jul. 15, 1986

[54] 1,2-DIHYDROPYRIDO[3,4-B]PYRAZINES

[75] Inventors: Carroll G. Temple; John A. Montgomery; Robert D. Elliott; Glynn P. Wheeler, all of Birmingham, Ala.

[73] Assignee: Southern Research Institute, Birmingham, Ala.

[21] Appl. No.: 716,945

[22] Filed: Mar. 28, 1985

Related U.S. Application Data

[63] Continuation-in-part of Ser. No. 362,480, Mar. 26, 1982, abandoned.

[51] Int. Cl.[4] .................. A61K 31/495; C07D 471/04; C07D 213/61
[52] U.S. Cl. .................. 514/249; 544/350; 546/308
[58] Field of Search .................. 544/350; 514/249

[56] References Cited

U.S. PATENT DOCUMENTS 4,450,160  5/1984  Temple, Jr. et al. .................. 544/350

FOREIGN PATENT DOCUMENTS 0061178  9/1982  European Pat. Off. ............. 544/350
0090681  10/1983  European Pat. Off. ............. 544/350

OTHER PUBLICATIONS

Wheeler, et al., "Chemical Abstracts", vol. 96, 1982, col. 96:79528s.
Hamel, et al., "Chemical Abstracts", vol. 96, 1982, col. 96:135450z.
Wheeler, et al., "Chemical Abstracts", vol. 96, 1982, col. 96:155154j.
Temple, et al., "Chemical Abstracts", vol. 97, 1982, col. 97:109969b.
Temple, et al., "Chemical Abstracts", vol. 100, 1984, col. 100:121106f.

Primary Examiner—Glennon H. Hollrah
Assistant Examiner—James H. Turnipseed
Attorney, Agent, or Firm—Roylance, Abrams, Berdo & Goodman

[57] ABSTRACT 1,2-Dihydropyrido[3,4-b]pyrazines are provided which possess anticancer activity. The compounds have the structure:

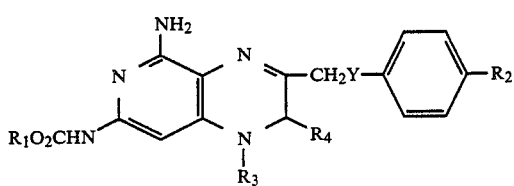

wherein Y is $CH_2$ or $N(CH_3)$; $R_1$ is a lower alkyl group; e.g., an alkyl group containing up to six carbon atoms such as methyl, ethyl, propyl, butyl, etc.; $R_2$ is a member selected from the group consisting of hydrogen, $CH_3O$ or Cl; and $R_3$ and $R_4$ are either both hydrogen or one is hydrogen and the other is a lower alkyl group.

8 Claims, No Drawings

1,2-DIHYDROPYRIDO[3,4-B]PYRAZINES

CROSS-REFERENCE TO RELATED APPLICATION

This application is a continuation-in-part of application Ser. No. 362,480, filed Mar. 26, 1982 now abandoned.

BACKGROUND OF THE INVENTION

This invention relates to novel 1,2-dihydropyrido[3,4-b]pyrazines, also known as 1-deaza-7,8-dihydropteridines. This invention also relates to a process for making such compounds and to novel intermediates obtained in said process.

The antimitotic chemical agents commonly known as spindle poisons are plant products of which the best known are colchicine, podophyllotoxin, and the vinca alkaloids. [L. Wilson, J. R. Bamburg, S. B. Mizel, L. M. Grisham and K. M. Creswell, *Federation Proceedings*, 33, 158 (1974)]. Two members of the latter, vincristine and vinblastine, are currently used clinically in the treatment of neoplasms. Although these agents produce a number of biochemical actions such as the inhibition of macromolecular synthesis, their primary effect is to prevent mitosis by interfering with the function of microtubules, which results in the accumulation of cells in metaphase. In addition, several benzimidazol-2-yl carbamates have been introduced as fungicides, anthelmintics and antitumoral agents. [L. C. Davidse and W. Flach, *J. Cell Biol.*, 72, 174 (1977)]. These compounds also prevent mitosis and their biological activity can probably be attributed to interference with the formation or functioning of microtubules.

The development of procedures for the preparation of 1-deazapteridines is reported by J. A. Montgomery and N. F. Wood, *J. Org. Chem.*, 29, 734 (1964); R. D. Elliott, C. Temple, Jr. and J. A. Montgomery, *J. Org. Chem.*, 33, 533 (1968); R. D. Elliott, C. Temple, Jr., J. L. Frye and J. A. Montgomery, *J. Org. Chem.*, 36, 2818 (1971); and R. D. Elliott, C. Temple, Jr. and J. A. Montgomery, *J. Med. Chem.*, 17, 553 (1974). These references disclose the preparation and use of various 1,2-dihydro[3,4-b]pyrazine derivatives. Thus, the 1964 *J. Org. Chem.* reference discloses the compounds:

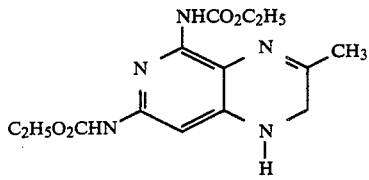

and

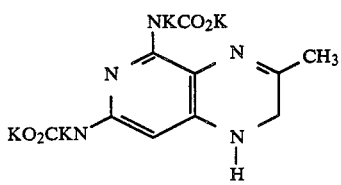

The 1968 *J. Org. Chem.* reference discloses the compound:

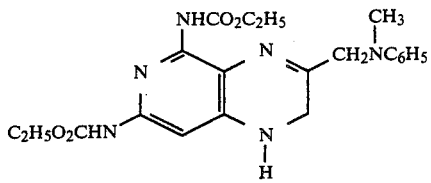

The 1971 *J. Org. Chem.* reference discloses the compounds:

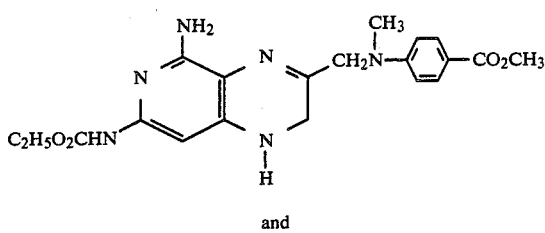

and

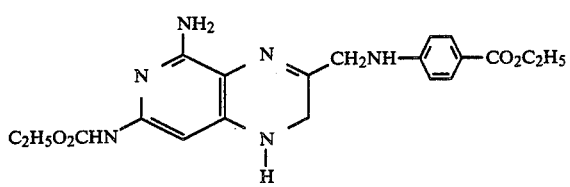

The *J. Med. Chem.* reference discloses that a dihydro-1-deazapteridine precursor of 1-deazamethotrexate showed activity against leukemia L1210 in mice. An abstract presented at the 28th Southeast Regional Meeting of the American Chemical Society in Gatlinburg, Tenn., Oct. 27–29, 1976 discloses that the compound

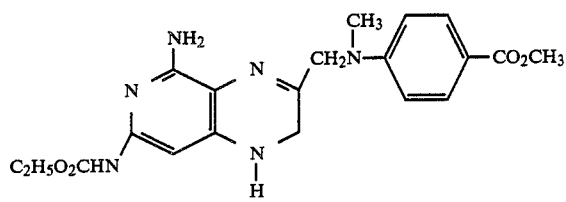

showed cytotoxicity in the KB cell culture screen and activity against leukemia L1210 in mice.

An abstract of a paper by B. J. Bowdon, G. P. Wheeler, C. G. Temple and J. A. Montgomery in AACR Abstracts, Vol. 22, March 1981 (page 25) discloses that a compound designated as "NSC-181928" was active against several neoplasms. NSC-181928 is the designation for the compound

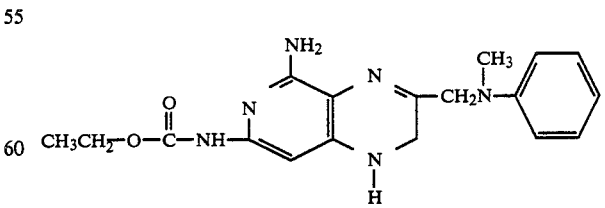

SUMMARY OF THE INVENTION

It has now been found that certain 1,2-dihydropyrido[3,4-b]pyrazines possess anticancer activity. The compounds of this invention have the structure:

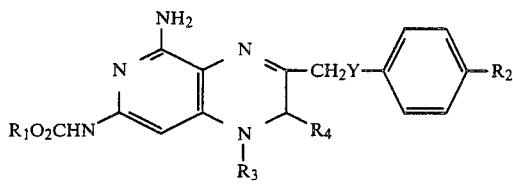

wherein Y is $CH_2$ or $N(CH_3)$; $R_1$ is a lower alkyl group, e.g., an alkyl group containing up to six carbon atoms such as methyl, ethyl, propyl, butyl, etc.; $R_2$ is a member selected from the group consisting of hydrogen, $CH_3O$ or Cl; and $R_3$ and $R_4$ are either both hydrogen or one is hydrogen and the other is a lower alkyl group, e.g., one containing 1 to 3 carbon atoms.

Compounds of Formula I wherein $R_3$ is hydrogen may be prepared by aminating a lower alkyl ester of 6-amino-4-chloro-5-nitropyridin-2-ylcarbamate having the structure:

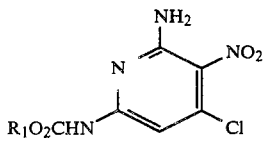

with the oxime of an alpha-amino ketone having the structure:

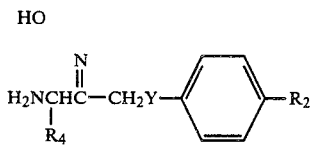

to give a compound having the structure:

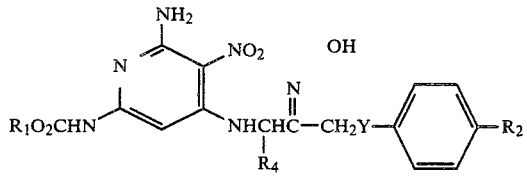

wherein $R_1$, $R_2$, $R_4$ and Y are the same as previously defined, further provided that $R_2$ may be a nitro group. The compound of Formula IV is hydrolyzed, e.g., by acid hydrolysis to give the corresponding ketone having the formula:

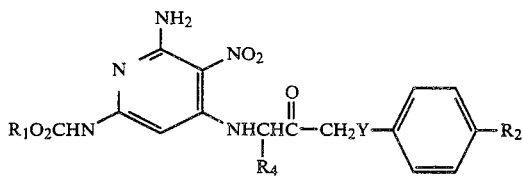

wherein $R_1$, $R_2$, $R_4$ and Y are the same as previously defined, further provided that $R_2$ may be a nitro group. The compound of Formula V is converted to the compound of Formula I by catalytic hydrogenation. An intermediate product formed during hydrogenation has the formula:

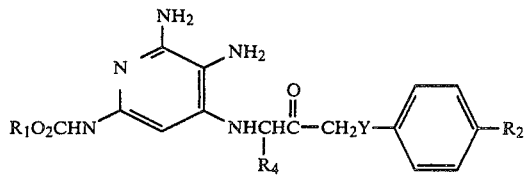

wherein $R_1$, $R_2$, $R_4$ and Y are the same as previously defined.

Compounds of Formula I wherein $R_4$ is hydrogen may be prepared by aminating the compound of Formula II with an alphaamino alcohol having the structure:

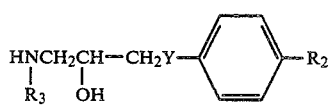

to give a compound having the structure:

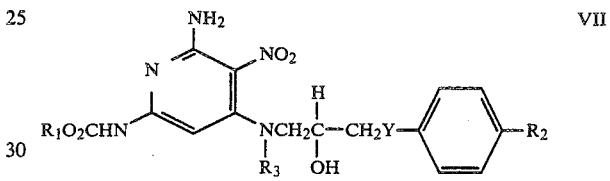

which is oxidized to give a ketone having the structure:

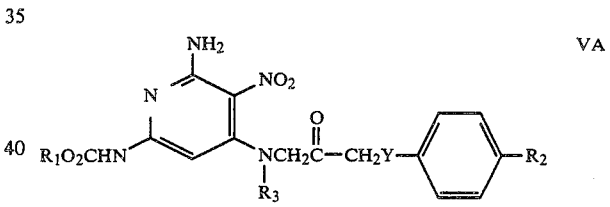

wherein $R_1$, $R_2$, $R_3$ and Y are the same as previously defined, further provided that $R_2$ may be a nitro group. The compound of Formula VA is converted to a compound of Formula I by catalytic hydrogenation.

DETAILED DESCRIPTION OF THE INVENTION

The compounds of the invention form pharmaceutically acceptable salts with both organic and inorganic acids. Examples of suitable acids for salt formation are hydrochloric, sulfuric, phosphoric, acetic, citric, oxalic, malonic, salicyclic, malic, fumaric, succinic, ascorbic, maleic, methanesulfonic, and the like. The salts are prepared by contacting the free base form with an equivalent amount of the desired acid in the conventional manner. The free base forms may be regenerated by treating the salt form with a base. For example, dilute aqueous base solutions may be utilized. Dilute aqueous sodium hydroxide, potassium carbonate, ammonia, and sodium bicarbonate solutions are suitable for this purpose. The free base forms differ from their respective salt forms somewhat in certain physical properties such as solubility in polar solvents, but the salts are otherwise equivalent to their respective free base forms for purposes of the invention.

Also embraced within the purview of the present invention are therapeutic compositions of matter useful for ameliorating cancer diseases in mammals and containing the 1-deaza-7,8-dihydropteridines of this invention or pharmaceutically acceptable salts thereof.

The active ingredients of the therapeutic compositions and the novel compounds of the present invention inhibit transplanted mouse tumor growth when administered in amounts ranging from about 5 mg to about 200 mg per kilogram of body weight per day. A preferred dosage regimen for optimum results would be from about 5 mg to about 50 mg per kilogram of body weight per day, and such dosage units are employed that a total of from about 350 mg to about 3.5 grams of the active compound for a subject of about 70 kg of body weight are administered in a 24-hour period. This dosage regimen may be adjusted to provide the optimum therapeutic response. For example, several divided doses may be administered daily or the dose may be proportionally reduced as indicated by the exigencies of the therapeutic situation. A decided practical advantage is that the active compound may be administered in any convenient manner such as by the oral, intravenous, intramuscular or subcutaneous routes.

The active compounds may be orally administered, for example, with an inert diluent or with an assimilable edible carrier, or they may be enclosed in hard or soft shell gelatin capsules, or they may be compressed into tablets, or they may be incorporated directly with the food of the diet. For oral therapeutic administration, the active compounds may be incorporated with excipients and used in the form of ingestible tablets, buccal tablets, troches, capsules, elixirs, suspensions, syrups, wafers and the like. Such compositions and preparations should contain at least 0.1% of active compound. The percentage of the compositions and preparations may, of course, be varied and may conveniently be between about 2 and about 60% of the weight of the unit. The amount of active compound in such therapeutically useful compositions is such that a suitable dosage will be obtained. Preferred compositions or preparations according to the present invention are prepared so that an oral dosage unit form contains between about 5 and about 200 milligrams of active compound.

The tablets, troches, pills, capsules and the like may also contain the following: a binder such as gum tragacanth, acacia, corn starch or gelatin; excipients such as dicalcium phosphate; a disintegrating agent such as corn starch, potato starch, alginic acid and the like; a lubricant such as magnesium stearate; and a sweetening agent such as sucrose, lactose or saccharin may be added or a flavoring agent such as peppermint, oil of wintergreen or cherry flavoring. When the dosage unit form is a capsule, it may contain, in addition to materials of the above type, a liquid carrier. Various other materials may be present as coatings or to otherwise modify the physical form of the dosage unit. For instance, tablets, pills or capsules may be coated with shellac, sugar or both. A syrup or elixir may contain the active compound, sucrose as a sweetening agent, methyl and propylparabens as preservatives, a dye and flavoring such as cherry or orange flavor. Of course, any material used in preparing any dosage unit form should be pharmaceutically pure and substantially non-toxic in the amounts employed. In addition, the active compounds may be incorporated into sustained-release preparations and formulations.

The active compounds may also be administered parenterally or intraperitoneally. Solutions of the active compound as a free base or pharmaceutically acceptable salt can be prepared in water suitably mixed with a surfactant such as hydroxypropylcellulose. Dispersions can also be prepared in glycerol, liquid polyethylene glycols, and mixtures thereof and in oils. Under ordinary conditions of storage and use, these preparations contain a preservative to prevent the growth of microorganisms.

The pharmaceutical forms suitable for injectable use include sterile aqueous solutions or dispersions and sterile powders for the extemporaneous preparation of sterile injectable solutions or dispersions. In all cases the form must be sterile and must be fluid to the extent that easy syringability exists. It must be stable under the conditions of manufacture and storage and must be preserved against the contaminating action of microorganisms such as bacteria and fungi. The carrier can be a solvent or dispersion medium containing, for example, water, ethanol, polyol (for example, glycerol, propylene glycol, and liquid polyethylene glycol, and the like), suitable mixtures thereof and vegetable oils. The proper fluidity can be maintained, for example, by the use of a coating such as lecithin, by the maintenance of the required particle size in the case of dispersion and by the use of surfactants. The prevention of the action of microorganisms can be brought about by various antibacterial and antifungal agents, for example, parabens, chlorobutanol, phenol, sorbic acid, thimerosal, and the like. In many cases, it will be preferable to include isotonic agents, for example, sugars or sodium chloride. Prolonged absorption of the injectable compositions can be brought about by the use in the compositions of agents delaying absorption, for example, aluminum monostearate and gelatin.

Sterile injectable solutions are prepared by incorporating the active compound in the required amount in the appropriate solvent with various of the other ingredients enumerated above, as required, followed by filtered sterilization. Generally, dispersions are prepared by incorporating the various sterilized active ingredient into a sterile vehicle which contains the basic dispersion medium and the required other ingredients from those enumerated above. In the case of sterile powders for the preparation of sterile injectable solutions, the preferred methods of preparation are vacuum drying and the freeze-drying technique which yield a powder of the active ingredient plus any additional desired ingredient from a previously sterile-filtered solution thereof.

As used herein, "pharmaceutically acceptable carrier" includes any and all solvents, dispersion media, coatings, antibacterial and antifungal agents, isotonic and absorption delaying agents and the like. The use of such media and agents for pharmaceutically active substances is well known in the art. Except insofar as any conventional media or agent is incompatible with the active ingredient, its use in the therapeutic compositions is contemplated. Supplementary active ingredients can also be incorporated into the compositions.

It is especially advantageous to formulate parenteral compositions in dosage unit form for ease of administration and uniformity of dosage. Dosage unit form as used herein refers to physically discrete units suitable as unitary dosages for the mammalian subjects to be treated; each unit containing a predetermined quantity of active material calculated to produce the desired therapeutic effect in association with the required pharmaceutical carrier. The specification for the novel dosage unit forms of the invention are dictated by and directly dependent on (a) the unique characteristics of the active material and the particular therapeutic effect to be achieved, and (b) the limitations inherent in the art of compounding such an active material for the treatment of disease in living subjects having a diseased condition in which bodily health is impaired as herein disclosed in detail.

The principal active ingredient is compounded for convenient and effective administration in effective amounts with a suitable pharmaceutically-acceptable carrier in dosage unit form as hereinbefore disclosed. A unit dosage form can, for example, contain the principal active compound in amounts ranging from about 0.1 to about 400 mg, with from about one to about 30 mg being preferred. Expressed in proportions, the active compound is generally present in from about 0.1 to about 400 mg/ml of carrier. In the case of compositions containing supplementary active ingredients, the dosages are determined by reference to the usual dose and manner of administration of the said ingredients.

A preferred lower alkyl ester of 6-amino-4-chloro-5-nitropyridin-2-ylcarbamate is the ethyl ester, i.e., ethyl 6-amino-4-chloro-5-nitropyridin-2-ylcarbamate. This compound is prepared according to the procedure described by R. D. Elliott, C. Temple, Jr. and J. A. Montgomery, *J. Org. Chem.*, 31, 1890 (1966).

Oximes of alpha-amino ketones, i.e., compounds of Formula III, may be prepared by known prior art procedures. Thus, they can be prepared by condensing the corresponding alpha-amino ketones with hydroxylamine hydrochloride in a refluxing mixture of pyridine and ethanol to give the oxime derivatives [R. D. Elliott, C. Temple, Jr. and J. A. Montgomery, *J. Org. Chem.*, 35, 1676 (1970)].

The compounds of Formula III can also be prepared by alkylation of phthalimide with the corresponding alpha-bromo-ketone, treatment of the alpha(phthalimido)-ketone product with hydroxylamine, and removal of the phthaloyl protecting group from the resulting oxime with hydrazine [R. D. Elliott, C. Temple, Jr. and J. A. Montgomery, *J. Org. Chem.*, 35, 1676 (1970)].

Examples of these two procedures for the preparation of compounds of Formula III follow:

METHOD I

1-Amino-3-[(N-methyl-N-phenyl)amino]propanone Oxime

A mixture of 1-bromo-3-(phthalimido)propanone (145 g, 514 mmol), N-methylaniline (55.1 g, 514 mmol) and NaHCO$_3$ (43.2 g, 514 mmol) in N,N-dimethyl acetamide (1450 ml) was stirred at room temperature for 24 hours followed by heating at 40° C. for 2 hours. The mixture was cooled in an ice bath and slowly diluted with cold water (440 ml). The yellow solid that precipitated was collected by filtration, washed with a 1:3 mixture of water-N,N-dimethyl acetamide (160 ml) and cold water, and dried in vacuo over P$_2$O$_5$: yield, 130 g. Dilution of the filtrate with additional water (1200 ml) gave a second crop of product: yield, 20.1 g. The combined crops (150 g) were recrystallized from ethanol to give the diaminopropanone in 3 crops: yield, 145 g. A solution of this product (474 mmol), hydroxylamine hydrochloride (49.3 g, 709 mmol) and pyridine (482 ml) in ethanol (200 ml) was refluxed for 2.5 hours and evaporated to dryness in vacuo. The residue was washed with cold water (2×500 ml), ethanol (250 ml) and recrystallized from ethanol to give the product in 3 crops: yield, 143 g. A solution of the resultant oxime (442 mmol) in ethanol (5300 ml) at 70° C. was treated dropwise during 20 minutes with a solution of 95% hydrazine (16.4 g) in ethanol (200 ml). The resulting solution was heated at 40° C. for 22 hours, and the cooled reaction mixture was treated with 1N HCl (485 ml). After stirring in an ice bath for 1 hour, the precipitated phthalhydrazide was removed by filtration and washed with 1:1 ethanol-water (600 ml). The combined filtrate and wash was evaporated to dryness in vacuo (40° C.), the residue was stirred with warm water (1500 ml), and after cooling, the insoluble yellow solid was removed by filtration and washed with water (200 ml). The clear yellow aqueous filtrate was treated with concentrated NH$_4$OH (35 ml), and the oil that separated was extracted with CHCl$_3$ (3×300 ml). The combined extracts were dried over Na$_2$SO$_4$ and evaporated to give a gum, which solidified on drying in vacuo over P$_2$O$_5$. The solid was pulverized, washed by vigorous stirring with cold water (700 ml), and redried in vacuo over P$_2$O$_5$ to give the α-aminoketone oxime as a mixture of syn and anti isomers: yield, 57.3 g.

METHOD II

1-Amino-4-phenyl-2-butanone Oxime

A solution of crude 1-amino-4-phenyl-2-butan-one hydrochloride (9.84 g, 49.2 mmol) (Degraw, J., Isakotellis, P., Kisliuk, R., and Gaumont, Y., *J. Heterocyclic Chem.*, 1971, 8, 105), hydroxylamine hydrochloride (6.84 g, 98.4 mmol) and sodium acetate. 3H$_2$O (13.4 g, 98.4 mmol) in 50% ethanol (250 ml) was heated at 75°–80° C. for 30 minutes, filtered, treated with a hot solution of picric acid (11.7 g, 51.1 mmol), cooled to 25° C., filtered and allowed to stand for 2 days. The crystalline picrate was collected, washed with 2:1 water-ethanol and dried in vacuo: yield 9.62 g, mp, 151° C. (Kofler Heizbank). The mother liquor was evaporated to dryness in vacuo, and the residue was crystallized from hot water (500 ml) to give an additional amount of the picrate: yield, 3.62 g, mp 151° C. A solution of the picrate in 3:1 ethanol-water (400 ml) was treated with washed BioRad AG1-X8 (Cl$^-$) ion exchange resin (100 g) and stirred for 18 hours. The solution was filtered and the resin was washed with 3:1 ethanol-water. The filtrate and wash were treated with additional resin (40 g), stirred for 2 hours and filtered. The almost colorless solution was evaporated with ethanol (3×200 ml). The residue was stirred with ethanol (100 ml), filtered and the precipitate was rinsed with additional ethanol (40 ml). The filtrate and wash were diluted with diethyl ether (600 ml) to give a crystalline hydrochloride which was collected, washed with diethyl ether and dried in vacuo (P$_2$O$_5$): yield, 5.36 g.

Alpha-amino alcohols of Formula IIIA are prepared by the following procedure:

METHOD III

1-Amino-3-[[N-(4-chlorophenyl)-N-methyl]amino]2-propanol

A solution of epichlorohydrin (11 ml) and 4-chloro-N-methylaniline (11 g, 78 mmol) in a mixture of ethanol (10 ml) and water (7 ml) was refluxed for 2 hours, diluted with water (20 ml), and extracted with diethyl ether (3×50 ml). The combined extracts were evaporated to dryness, the residue was treated with a solution of NaOH (5 g) in water (10 ml) for 1 hour, and the resulting mixture was extracted with diethyl ether (4×25 ml). The combined extracts were dried (MgSO$_4$) and evaporated to dryness in vacuo to give 1-[[N-(4-chlorophenyl)-N-methyl]amino]-2,3-epoxypropane: yield, 11 g (72%). A solution of this sample in a mixture of ethanol (50 ml) and liquid NH$_3$ (20 ml) was heated in a glass-lined stainless steel bomb at 100° C. for 3 hours. The resulting reaction solution was evaporated to dryness, and the dried residue was recrystallized from C$_6$H$_5$: yield, 5.3 g (44%).

The oximes and alpha-amino alcohols set forth in Table I were prepared by Method I, Method II or Method III, as indicated in Table I. The first column of Table I sets forth the structure of the group

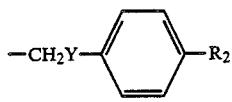

in Formula III for the oximes prepared by Methods I and II and in Formula IIIA for the alpha-amino alcohol prepared by Method III.

EXAMPLE 1

Ethyl 6-Amino-4-[3-[(N-methyl-N-phenyl)amino]-2-oxo-propylamino]-5-nitro-2-pyridinecarbamate Oxime (IV: R$_1$=C$_2$H$_5$; R$_2$=H; R$_4$=H; Y=N(CH$_3$))

A solution of ethyl 6-amino-4-chloro-5-nitro-2-pyridinecarbamate (10.3 g, 30.5 mmol), 1-amino-3-[(N-methyl-N-phenyl)propanone oxime (7.77 g, 40.2 mmol) and triethylamine (4.27 g, 42.2 g, 42.2 mmol) in ethanol (200 ml) was heated under N$_2$ at 75° C. for 24 hours. After cooling the reaction mixture the yellow solid was collected by filtration, washed with cold ethanol, and dried in vacuo over P$_2$O$_5$ at 65° C.: yield, 13.8 g. The properties of the compound thus obtained are set forth in Table II.

Additional compounds were prepared similarly wherein the oxime of Example 1 was replaced with other oximes. The properties of these compounds are set forth in Table II. The first column of Table II sets forth the structure of the group:

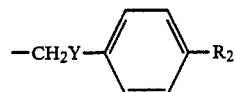

TABLE I

Alpha-Aminoketone Oximes (III) and Alpha-Aminoalcohols (IIIA)

| Compound[a] | Method | Yield, %[b] | M.p. °C. | Formula | Calcd, % C | H | N | Found, % C | H | N |
|---|---|---|---|---|---|---|---|---|---|---|
| C$_6$H$_5$N(CH$_3$)CH$_2$ (R$_4$ = H) | I | 56 | c | C$_{10}$H$_{15}$N$_3$O.0.33H$_2$O | 60.30 | 7.93 | 21.09 | 60.43 | 7.61 | 21.01 |
| 4-CH$_3$OC$_6$H$_4$N(CH$_3$)CH$_2$ (R$_4$ = H) | I | 28 | c | C$_{11}$H$_{17}$N$_3$O.0.37H$_2$O | 57.46 | 7.78 | 18.27 | 57.39 | 7.70 | 18.38 |
| 4-CH$_3$OC$_6$H$_4$N(CH$_3$)CH$_2$ (R$_4$ = CH$_3$) | I | 27 | 141–8 | C$_{12}$H$_{19}$N$_3$O$_2$.2HCl.1.4H$_2$O[d] | 42.96 | 7.17 | 12.53 | 43.39 | 7.19 | 12.49 |
| C$_6$H$_5$CH$_2$CH$_2$ (R$_4$ = H) | II | 50 | 193 | C$_{10}$H$_{14}$N$_2$O.HCl.0.3H$_2$O | 54.82 | 6.72 | 12.79 | 54.63 | 7.00 | 12.58 |
| 4-ClC$_6$H$_4$N(CH$_3$)CH$_2$ (R$_4$ = H) | III | 32 | 117–9[e] | C$_{10}$H$_{15}$ClN$_2$O | 55.95 | 7.04 | 13.05 | 56.29 | 7.18 | 13.17 |

[a]R$_3$ = H
[b]Overall yield
[c]Indefinite melting point
[d]Dihydrochloride salt was generated in ethanolic hydrogen chloride and precipitated with ether
[e]Resolidified and remelted at 123° C.

A compound of Formula II is aminated with a compound of Formula III under nitrogen in refluxing ethanol containing triethylamine as an acid acceptor to give a compound of Formula IV. An example of this procedure follows:

in the starting alpha-aminoacetophenone oxime, see Formula III wherein R$_1$ is C$_2$H$_5$ and R$_4$ is H or CH$_3$, and in the final product, see Formula IV, wherein R$_1$ is C$_2$H$_5$ and R$_4$ is H or CH$_3$.

TABLE II

Ethyl 4-(Substituted)amino-6-amino-5-nitro-pyridine-2-carbamate Oximes

| Compound | Reaction Time, Hours | Yield, % | M.p. °C. | Formula | Calcd, % C | H | N | Found, % C | H | N |
|---|---|---|---|---|---|---|---|---|---|---|
| C$_6$H$_5$N(CH$_3$)CH$_2$ (R$_4$ = H) | 24 | 84 | 192-3 dec | C$_{18}$H$_{23}$N$_7$O$_5$ | 51.79 | 5.55 | 23.49 | 51.77 | 5.65 | 23.69 |
| 4-CH$_3$OC$_6$H$_4$N(CH$_3$)CH$_2$ (R$_4$ = H) | 15[a] | 75 | 190 | C$_{19}$H$_{25}$N$_7$O$_6$ | 51.00 | 5.63 | 21.91 | 50.97 | 5.89 | 21.87 |
| 4-CH$_3$OC$_6$H$_4$N(CH$_3$)CH$_2$ (R$_4$ = CH$_3$) | 16 | 77 | — | C$_{20}$H$_{27}$N$_7$O$_6$.2HCl.H$_2$O[b] | 43.48 | 5.66 | 17.75 | 43.53 | 5.30 | 17.65 |
| C$_6$H$_5$CH$_2$CH$_2$ (R$_4$ = H) | 24[c] | 84 | 187 | C$_{18}$H$_{22}$N$_6$O$_5$ | 53.72 | 5.51 | 20.89 | 53.61 | 5.56 | 20.77 |

[a]Solvent, methanol
[b]Dihydrochloride salt prepared from a solution of the base in a mixture of benzene and chloroform by the addition of ethanolic hydrogen chloride
[c]Reaction temperature 54° C.

Treatment of a compound of Formula IV with a 1:1 mixture of 1N hydrochloric acid and dioxane at 60° C.

hydrolyzes the oxime function to give a compound of Formula V. An example of this procedure follows:

EXAMPLE 2

Ethyl 6-Amino-4-[2-oxo-4-(phenylbutyl)amino]-5-nitro-2-pyridinecarbamate (V: $R_1=C_2H_5$; $R_2=H$; $R_4=H$; $Y=CH_2$)

A solution of the oxime of the title compound (6.17 g, 15.4 mmol) in warm dioxane (60 ml) was treated with 1N HCl (120 ml), stirred at 55° C. for 1 hour and cooled in an ice bath. The precipitated hydrochloride was collected, washed with cold water, then suspended in water (300 ml) and neutralized with 1N NaOH. The yellow product was collected, washed with water and dried in vacuo ($P_2O_5$): yield, 5.08 g (83%); m.p. 155° C. Anal. Calcd. for $C_{18}H_{21}N_5O_5$: C, 55.80; H, 5.46; N, 18.08. Found: C, 55.42; H, 5.49; N, 18.12.

Amination of the compound of Formula II with the compound of Formula IIIA in refluxing ethanol containing triethylamine as an acid acceptor gives a compound of Formula VII. Oxidation of a compound of Formula VII gives a ketone of Formula VA. Two examples of this procedure follow:

EXAMPLE 3

A. Ethyl 6-Amino-4-[3-[[N-(4-chlorophenyl)-N-methyl]amino]-2-hydroxypropylamino]-5-nitro-2-pyridinecarbamate (VII: $R_1=C_2H_5$; $R_2=4$-Cl; $R_3=H$; $Y=N(CH_3)$)

A solution of ethyl 6-amino-4-chloro-5-nitro-2-pyridinecarbamate (10.0 g), 1-amino-3-[[N-(4-chlorophenyl)-N-methyl]amino]-2-propanol (8.25 g), and triethylamine (10.7 ml) in methanol (120 ml) was heated at 60° C. for 18 hours and evaporated to dryness in vacuo. The dark residue was washed with diethyl ether (1.5 l) to give a yellow solid. This solid was washed with water (50 ml) and recrystallized twice from a mixture of ethanol and hexane: yield, 4.92 g. Similar treatment of the residue obtained from the ether wash from above gave a slightly impure sample of product: yield, 5.89 g. Total yield, 10.81 g (64%); m.p., 181° C. Anal. Calcd. for $C_{18}H_{23}ClN_6O_5$: C, 49.26; H, 5.28; N, 19.15. Found: C, 49.16; H, 5.46; N, 19.22.

B. Ethyl 6-Amino-4-[3-[[N-(4-chlorophenyl)-N-methyl]amino]-2-oxopropylamino]-5-nitro-2-pyridinecarbamate (VA: $R_1=C_2H_5$; $R_2=4$-Cl; $R_3=H$; $Y=N(CH_3)$)

A solution of ethyl-6-amino-4-[3-[[N-(4-chlorophenyl)-N-methyl]amino]-2-hydroxypropylamino]-5-nitro-6-pyridinecarbamate (1.76 g) and acetic anhydride (8 ml) in dimethyl sulfoxide (40 ml) was stirred at room temperature for 20 hours, diluted with water (200 ml), and neutralized to pH 5.2 with 1N NaOH. The solid that deposited was collected by filtration and dissolved in CHCl$_3$. Evaporation of this solution to dryness and trituration of the resulting solid successively with water and ethanol gave the product: yield, 0.36 g (20%); m.p. 123°–5° C. Anal. Calcd. for $C_{18}H_{21}ClN_6O_5 \cdot 0.5H_2O$: C, 48.49; H, 4.97; N, 18.85. Found: C, 48.74; H, 4.65; N, 18.89.

EXAMPLE 4

A. Ethyl 6-Amino-4-[3-[(N-methyl-N-phenyl)amino]-2-hydroxyoxopropylamino]-5-nitro-2-pyridinecarbamate (VII: $R_1=C_2H_5$; $R_2=H$; $R_3=H$; $Y=N(CH_3)$)

This compound was prepared by the procedure described in Example 3A, substituting 1-amino-3-[(N-methyl-N-phenyl)amino]-2-propanol [O. Eisleb, German Pat. No. 473,219 (1926); Chem. Zentra., 100 (II), 350 1929)] for 1-amino-3-[[N-(4-chlorophenyl)-N-methyl]-amino]-2 propanol: yield, 73%; m.p., 88°–90° C. Anal. Calcd. for $C_{18}H_{24}N_6O_5$: C, 53.46; H, 5.98; N, 20.78. Found: C, 53.63; H, 5.93; N, 20.81.

B. Ethyl 6-Amino-4-[3-[(N-methyl-N-phenyl)amino]-2-oxopropylamino]-5-nitro-2-pyridinecarbamate (VA: $R_1=C_2H_5$; $R_2=H$; $R_3=H$; $Y=N(CH_3)$)

Crystalline o-phosphoric acid (3.08 g, 31.5 mmol) was added to a stirred solution of ethyl 6-amino-4-[3-[(N-methyl-N-phenyl)amino]-2-hydroxypropylamino]-5-nitro-2-pyridinecarbamate (3.18 g, 7.87 mmol) and N,N'-dicylohexylcarbodiimide (4.86 g, 23.6 mmol) in dry dimethyl sulfoxide (40 ml). The mildly exothermic reaction was kept below 25° C. by water bath cooling. After 2.5 hours, the deposit of dicyclohexylurea was filtered off and washed with dimethyl sulfoxide (25 ml). The filtrate was cooled in an ice bath and diluted slowly with water (100 ml) to precipitate the product as a bright yellow solid that was washed thoroughly with water and dried in vacuo over $P_2O_5$: yield, 2.89 g (80%); m.p., ~80° C. with presoftening. Anal. Calcd. for $C_{18}H_{22}N_6O_5 \cdot H_2O \cdot 0.5(CH_3)_2SO$: C, 49.67; H, 5.92; N, 18.29. Found: C, 49.82; H, 5.69; H, 18.06.

The catalytic hydrogenation of a compound of Formula V or VA with a three-fold amount of Raney nickel in a large volume of ethanol (i.e., more than one liter per gram) at atmospheric pressure at room temperature or with intermittent warming (e.g., to no higher than 60° C.) with a water bath gives the intermediate compound of Formula VI which is cyclized in situ with the elimination of water to give a compound of Formula I. Such reaction is shown in Example 5. The compounds of Formula I can also be prepared directly by hydrogenation of a compound of Formula IV in the presence of Raney nickel as shown in Examples 6 and 7.

EXAMPLE 5

Ethyl 5-Amino-1,2-dihydro-3-(2-phenylethyl)pyrido(3,4-b)pyrazine-7-carbamate (I: $R_1=C_2H_5$; $R_2=4$-CH$_3$O; $R_3=H$; $R_4=H$; $Y=CH_2$)

A solution of ethyl 6-amino-4-amino-4-[2-oxo-4-(phenylbutyl)amino]-5-nitro-2-pyridinecarbamate (300 mg, 0.775 mmol) in N,N'-dimethyl acetamide (7 ml) was hydrogenated in the presence of Raney nickel (890 mg, weighed wet, washed with ethanol) for 20 hours to give an H$_2$ uptake of 58 ml (3.07 mmol). The reaction mixture was filtered under N$_2$ and evaporated in vacuo at 25° C. The residual syrup was stirred with water (10 ml) to give a white powder which was collected, washed with water and dried in vacuo ($P_2O_5$): yield, 230 mg. The properties are set forth in Table III.

EXAMPLE 6

Ethyl 5-Amino-1,2-dihydro-3-[(N-methyl-N-pheny)aminomethyl]pyrido[3,4-b]pyrazine-7-carbamate (I: $R_1=C_2H_5$; $R_2=H$; $R_3=H$; $R_4=H$; $Y=N(CH_3)$)

A suspension of the oxime of ethyl 6-amino-4-[3-[(N-methyl-N-phenyl)amino]-2-oxopropylamino]-5-nitro-2-pyridinecarbamate (30.0 g, 71.9 mmol) and Raney nickel (60 g, weighed wet, washed with ethanol) in ethanol (3000 ml) was hydrogenated at room temperature and atmospheric pressure with vigorous stirring. At the end of 12 hours, the hydrogen (7048 ml) absorbed corresponded to 134% of the theoretical for 4 molar equivalents. The resulting mixture was heated nearly to boiling under an atmosphere of $N_2$, and the catalyst was removed by filtration and washed with boiling ethanol (5×200 ml). The combined filtrate and wash were concentrated to about 1000 ml in vacuo and cooled in an ice bath to deposit the product as a pale yellow crystalline solid: yield, 16.7 g. The properties are set forth in Table III.

EXAMPLE 7

Ethyl 5-Amino-1,2-dihydro-3-[[N-(4-methoxyphenyl)-N-methylamino]methyl]-2-methylpyrido[3,4-b]pyrazine-7-carbamate

[I: $R_1=C_2H_5$; $R_2=4$-$CH_3O$; $R_3=H$; $R_4=CH_3$; $Y=N(CH_3)$]

A suspension of the oxime of ethyl 6-amino-4-[3-[[N-(4-methoxyphenyl)-N-methyl]amino]-1-methyl-2-oxopropylamino]-5-nitro-2-pyridinecarbamate (500 mg, 1.08 mmol) and Raney nickel (1.8 g, weighed wet, washed with ethanol) in ethanol (500 ml) was hydrogenated at room temperature and atmospheric pressure. After 48 hours, thin layer chromatography showed the absence of the oxime starting material. The catalyst was removed by filtration, and the filtrate was concentrated in vacuo to ¼ volume. The resulting solution was diluted with an equal volume of deoxygenated water to deposit the product: yield, 138 mg.

The compounds set forth in Table III were prepared by the procedure of Example 5, Example 6 or Example 7, as indicated in Table III. The properties of these compounds are set forth in Table III. The first column of Table III sets forth the structure of the group:

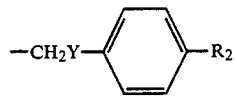

in the starting material, see Formulas IV, V and VA wherein $R_2$ is $C_2H_5$, $R_3$ is hydrogen and $R_4$ is hydrogen or methyl, and in the final product, see Formula I wherein $R_1$ is $C_2H_5$, $R_3$ is hydrogen and $R_4$ is hydrogen or methyl.

TABLE III

Ethyl 3-Substituted 5-Amino-1,2-dihydropyrido-[3,4-b]pyrazine-7-carbamates

| | Procedure of Example | Reaction Time, Hours | Yield, % | M.p. °C. | Formula | Analyses Calcd, % | | | Found, % | | |
|---|---|---|---|---|---|---|---|---|---|---|---|
| Compound | | | | | | C | H | N | C | H | N |
| $C_6H_5N(CH_3)CH_2$ ($R_4 = H$) | 6 | 12 | 63 | 165[a] | $C_{18}H_{22}N_6O_2 \cdot 0.3H_2O \cdot 0.15C_2H_6O$ | 59.94 | 6.46 | 22.92 | 59.98 | 7.05 | 22.92 |
| $C_6H_5N(CH_3)CH_2$ ($R_4 = H$) | 5 | 42 | 32 | 80[b] | $C_{18}H_{22}N_6O_2 \cdot 0.5C_2H_6O$ | 60.46 | 6.68 | 22.26 | 60.42 | 6.45 | 22.67 |
| 4-$ClC_6H_4N(CH_3)CH_2$ ($R_4 = H$) | 5 | 20 | 16 | a | $C_{18}H_{21}ClN_6O_2 \cdot 0.5H_2O \cdot 0.5C_2H_6O$ | 54.22 | 5.99 | 19.97 | 54.06 | 5.96 | 19.83 |
| 4-$CH_3OC_6H_4N(CH_3)CH_2$ ($R_4 = H$) | 6 | 3 | 73 | 187 | $C_{19}H_{24}N_6O_3$ | 59.36 | 6.29 | 21.86 | 59.16 | 6.29 | 21.88 |
| 4-$CH_3OC_6H_4N(CH_3)CH_2$ ($R_4 = CH_3$) | 7 | 48 | 31 | c | $C_{20}H_{26}N_6O_3 \cdot 0.15H_2O \cdot 0.3C_2H_6O$ | 59.62 | 6.83 | 20.25 | 59.59 | 6.86 | 20.15 |
| $C_6H_5CH_2CH_2$ ($R_4 = H$) | 5 | 20 | 88 | 163 | $C_{18}H_{21}N_5O_2$ | 63.70 | 6.24 | 20.64 | 63.35 | 6.25 | 20.47 |

[a]prior sintering;
[b]sintering;
[c]indefinite

The 1,2-dihydropyrido[3,4-b]pyrazines of this invention are powerful inhibitors of the proliferation of cultured lymphoid luekemia L1210 cells as shown in Table IV. The concentration causing a 50% inhibition of proliferation of the cells during 24 hours is similar to that observed for vincristine, vinblastine, and colchicine. Also, the addition to the test medium of inosine, thymidine, glycine, citrovorum factor, individually and in combinations, and elevated concentrations of amino acids and vitamins did not overcome the inhibitions.

In addition to cell cytotoxicity, the 1,2-dihydropyrido[3,4-b]pyrazines showed activity against lymphocytic leukemia P388 cells ($10^6$) implanted intraperitoneally in mice. Ethyl 5-amino-1,2-dihydro-3-[(N-methyl-N-phenyl)aminomethyl]pyrido[3,4-b]pyrazine-7-carbamate and ethyl 5-amino-1,2-dihydro-3-[[(N-(4-methoxyphenyl)-N-methyl]aminomethyl]pyrido[3,4-b]pyrazine-7-carbamate are also active in mice against P388 cells that were resistant to vincristine.

The 1,2-dihydropyrido[3,4-b]pyrazines of this invention at concentrations that prevented any increase in the cell number during a 24 hour period had little effect upon the synthesis of DNA, RNA, and protein by cultured L1210 cells during exposure for four hours. This result and those described above led to the determination of the effect of the 1,2-dihydropyrido[3,4-b]pyrazines upon cell division. Exposure of cultured L1210 cells to the 1,2-dihydropyrido[3,4-b]pyrazines inhibited cell division as measured by the mitotic index (MI) (Table IV), which is the fraction of the cell population that is made up of metaphase cells. Subsequent experiments showed that these agents caused the accumulation in metaphase of human epidermoid carcinoma #2 cells, P388 cells, and P388 cells resistant to vincristine grown in suspension culture and of colon tumor #26 cells and colon tumor #38 cells grown on plastic surfaces.

Table IV sets forth biological data for 1-deaza-7,8-dihydropteridines of this invention and for two prior art compounds. The first column of Table IV sets forth the structure of the group R in the formula in the heading of the table for the 1-deaza-7,8-dihydropteridines tested and the meaning of R.

The data in Table IV shows that the 1-deaza7,8-dihydropteridines of this invention are active against leukemia in laboratory animals.

TABLE IV

Biological Data - 1-Deaza-7,8-dihydropteridines

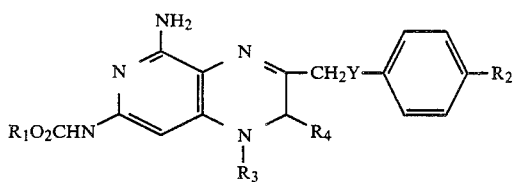

| Compound | L1210(a) ID$_{50}$ μM | Mitotic Index(b) 12 h (μM) | Mitotic Index(b) 24 h (μM) | P388(c) 10$^6$ Tumor cell implant, i.p. Schedule, Days | P388(c) 10$^6$ Tumor cell implant, i.p. % ILS (mg/kg) |
|---|---|---|---|---|---|
| Nocodazole | 27 × 10$^{-3}$ |  | 0.19(0.3) |  |  |
| Vincristine | 1 × 10$^{-3}$ |  | 0.62(0.3) | 1 | 100(2.7) |
| R = C$_6$H$_5$N(CH$_3$)CH$_2$ (R$_4$ = H) | 8.4 × 10$^{-3}$(d) | 0.77(0.03) | 0.80(0.3) | 1 1(e) 1(g) | 114(100) 66(100)(f) 90(67) |
| R = 4-CH$_3$OC$_6$H$_4$N(CH$_3$)CH$_2$ (R$_4$ = H) | 7.9 × 10$^{-3}$(h) | 0.64(0.03) 0.49(0.3) |  | 1 1 1(g) | 80(50)(i) 133(25) 150(25) |
| R = 4-CH$_3$OC$_6$H$_4$N(CH$_3$)CH$_2$ (R$_4$ = CH$_3$) | 5.5 × 10$^{-3}$ | 0.66(0.3) |  | 1-5 | 53(48) |
| R = 4-ClC$_6$H$_4$N(CH$_3$)CH$_2$ (R$_4$ = H) | 14.5 × 10$^{-3}$ | 0.71(0.03) |  | 1 | 65(100) |
| R = C$_6$H$_5$CH$_2$CH$_2$ (R$_4$ = H) | 13 × 10$^{-3}$ |  | 0.33(0.3) | 1 | 29(100) |
| R = 4-CH$_3$O$_2$CC$_6$H$_4$N(CH$_3$)CH$_2$(j) (R$_4$ = H) | 58 × 10$^{-3}$ | 0.61(0.3) 0.44(0.1) |  | 1-9 | 30(25) |

(a)Concentration of agent that inhibits proliferation of cultured lymphoid leukemia L1210 cells to 50% control growth during 48 hours. G. P. Wheeler, B. J. Bowdon, J. A. Werline, D. J. Adamson and C. Temple, Jr., Cancer Res., 42, 791 (1982).
(b)Fraction of the cell population of cultured lymphoid leukemia L1210 cells in mitosis [ref in a].
(c)Lymphocytic leukemia P388. R. I. Geran, N. H. Greenbert, M. M. MacDonald, A. M. Schumacker, and B. J. Abbott, Cancer Chemother. Rep., 3 (2) (1972).
(d)Average of 2-determinations.
(e)Methotrexate-resistant line of P388 (designated tumor P7 by the Drug Evaluation Branch, National Cancer Institute). In mice with 10$^6$ cell implant (IP), methotrexate at a dose of 2 mg/kg on the qd 1-9 schedule gave a 2-log cell kill against the sensitive line of P388 and a 2-log increase in cells against the methotrexate-resistant line of P388.
(f)1-cure.
(g)Vincristine-resistant line of P388. L. J. Wilkoff and E. A. Dulmadge, J. Natl. Cancer Inst., 61, 1521 (1978).
(h)Average of 2-determinations.
(i)2-cures.
(j)R. D. Elliott, C. Temple, Jr., J. L. Frye, and J. A. Montgomery, J. Org. Chem., 36, 2818 (1971).

We claim:

1. A 1,2-dihydropyrido[3,4-b]pyrazine having the formula:

wherein Y is CH$_2$ or N(CH$_3$); R$_1$ is a lower alkyl group; R$_2$ is a member selected from the group consisting of hydrogen, CH$_3$O or Cl; R$_3$ and R$_4$ are either both hydrogen or one is hydrogen and the other is a lower alkyl group; and pharmaceutically acceptable salts thereof.

2. A compound as defined in claim 1 wherein R$_1$ is ethyl.

3. Ethyl 5-amino-1,2-dihydro-3-[[N-(4-methoxyphenyl)-N-methylamino]methyl]-2-methylpyrido[3,4-b]pyrazine-7-carbamate.

4. Ethyl 5-amino-1,2-dihydro-3-[(N-methyl-N-phenyl)-aminomethyl]pyrido[3,4-b]pyrazine-7-carbamate.

5. Ethyl 5-amino-1,2-dihydro-3-[[N-(4-methoxyphenyl)-N-methyl]aminomethyl]pyrido[3,4-b]pyrazine-7-carbamate.

6. Ethyl 5-amino-1,2-dihydro-3-[[N-(4-chlorophenyl)-N-methyl[aminomethyl]pyrido[3,4-b]pyrazine-7-carbamate.

7. Ethyl 5-amino-1,2-dihydro-3-(2-phenylethyl)-pyrido[3,4-b]pyrazine-7-carbamate.

8. A pharmaceutical composition in dosage unit form comprising an effective amount to ammeliorate cancer diseases in mammals of a compound as defined by claim 1 in association with a pharmaceutical carrier.

* * * * *